United States Patent
Fritz et al.

(10) Patent No.: US 9,247,982 B2
(45) Date of Patent: Feb. 2, 2016

(54) SUPPLY DEVICE FOR OPERATION OF AT LEAST ONE MEDICAL INSTRUMENT, METHOD FOR GENERATION OF A CONTROL PROGRAM

(75) Inventors: Martin Fritz, Tuebingen (DE); Heiko Schall, Nuertingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 407 days.

(21) Appl. No.: 13/497,108

(22) PCT Filed: Sep. 21, 2010

(86) PCT No.: PCT/EP2010/005776
§ 371 (c)(1),
(2), (4) Date: Mar. 20, 2012

(87) PCT Pub. No.: WO2011/032729
PCT Pub. Date: Mar. 24, 2011

(65) Prior Publication Data
US 2012/0184948 A1    Jul. 19, 2012

(30) Foreign Application Priority Data
Sep. 21, 2009   (DE) .......................... 10 2009 042 428

(51) Int. Cl.
| | | |
|---|---|---|
| *A61B 18/00* | (2006.01) | |
| *A61B 18/02* | (2006.01) | |
| *A61B 17/3203* | (2006.01) | |
| *A61B 18/14* | (2006.01) | |
| *A61B 18/12* | (2006.01) | |

(52) U.S. Cl.
CPC ................ *A61B 18/00* (2013.01); *A61B 18/12* (2013.01); *A61B 18/1482* (2013.01); *A61B 2018/00083* (2013.01); *A61B 2018/00958* (2013.01)

(58) Field of Classification Search
USPC .......................................... 607/99; 606/41–42
See application file for complete search history.

(56) References Cited

U.S. PATENT DOCUMENTS

| | | | |
|---|---|---|---|
| 5,309,919 A | 5/1994 | Snell et al. | |
| 7,738,971 B2 | 6/2010 | Swayze et al. | |
| 8,632,535 B2 | 1/2014 | Shelton, IV et al. | |
| 2003/0046658 A1* | 3/2003 | Raghavan et al. | 717/106 |
| 2003/0237027 A1 | 12/2003 | Cook | |
| 2007/0179495 A1* | 8/2007 | Mitchell et al. | 606/41 |
| 2010/0125292 A1* | 5/2010 | Wiener et al. | 606/169 |

FOREIGN PATENT DOCUMENTS

| | | |
|---|---|---|
| CN | 101224117 A | 7/2008 |
| CN | 101361666 A | 2/2009 |
| DE | 10 2005 025 946 A1 | 8/2006 |
| DE | 10 2008 061 418 A1 | 6/2009 |

(Continued)

*Primary Examiner* — Carl H Layno
*Assistant Examiner* — Jon Eric C Morales
(74) *Attorney, Agent, or Firm* — Dickstein Shapiro LLP

(57) ABSTRACT

A supply device for the operation of at least one medical instrument, in particular an electrosurgical instrument and/or a cryosurgical instrument and/or a water jet surgical instrument. The supply device includes a control unit for the control of the at least one medical instrument and a memory unit for the storage of configuration data which describe a state device with a plurality of states. The control unit is designed such that it reads in configuration data and converts the state device into a control program and controls the at least one medical instrument according to the control program. This ensures efficient control of medical instruments because the control programs used can be more efficiently checked for their correctness and updated accordingly.

20 Claims, 2 Drawing Sheets

(56) References Cited

FOREIGN PATENT DOCUMENTS

| | | |
|---|---|---|
| DE | 10 2008 048 686 A1 | 4/2010 |
| DE | 10 2009 017 616 A | 5/2010 |
| EP | 1 829 493 A1 | 9/2007 |
| EP | 1 862 137 A1 | 12/2007 |
| WO | WO 96/13216 A1 | 5/1996 |
| WO | WO 03/090849 A1 | 11/2003 |
| WO | WO 2009/041912 A1 | 4/2009 |

* cited by examiner

SUPPLY DEVICE FOR OPERATION OF AT LEAST ONE MEDICAL INSTRUMENT, METHOD FOR GENERATION OF A CONTROL PROGRAM

FIELD OF THE INVENTION

Embodiments of the invention relate to a supply device for operating at least one medical instrument and a method for generating a control program.

BACKGROUND

In recent years, control technology has become increasingly important in the field of medicine. Devices that include a large number of electronic components are used in numerous operations. These medical devices usually include at least one instrument and a supply device that supplies the instrument accordingly. For example, electronically-controlled cryosurgical, electrosurgical and water jet surgical instruments are known and are operated by very complex control algorithms. For example, in high-frequency surgery (HF surgery) alternating current of high frequency is passed through the human body to devitalize or cut tissue in a targeted manner. In HF surgery, an HF generator is connected to a corresponding electrosurgical instrument to provide a suitable alternating current. In cryosurgery, supply devices, which are in fluid connection with corresponding instruments (for example, cryoprobes), provide a fluid for cooling the instrument. The corresponding supply devices must have control units, input units and output units to control the connected instruments in a suitable manner.

Corresponding electrosurgical devices are disclosed in European Patent Applications EP 1 862 137 A1 and EP 1 829 493 A1. A number of parameters (e.g., tissue type, operating mode, etc.) have to be taken into consideration for the control of these devices. The control units contained in the supply devices control various variables (e.g., voltage, current, power and modulation frequency, etc.). Electrosurgical supply devices often provide a number of operating modes, for example, a mode for cutting and a mode for coagulation.

In the past, a separate control program was developed for each of these operating modes. Maintenance of these programs is extremely time-consuming and susceptible to errors. Furthermore, the correctness of corresponding control programs cannot be established deterministically, meaning that numerous tests are necessary to ensure the safety of both the patient to be treated and the personnel. The development of control programs is therefore very expensive.

SUMMARY

An object of the embodiments of the present invention is to provide a supply device which can be easily programmed and which ensures verification of the correctness of the program quickly and efficiently. Furthermore, a method for generating a control program for a corresponding supply device is also provided.

In particular, the object is achieved by a supply device for operating at least one medical instrument, in particular an electrosurgical instrument and/or a cryosurgical instrument and/or a water jet surgical instrument, where the supply device includes: a control unit to control the at least one instrument; a memory unit for saving configuration data describing a state machine (i.e., device) having a plurality of states; the control unit being designed such that it reads in the configuration data, converts the state machine into a control program and controls the at least one instrument according to the control program.

An aspect of the present invention is therefore to provide a framework program or framework within the supply device which enables reading-in and implementation of a control program for the instruments in the form of a state machine. This framework program does not normally have to be changed to further develop the functioning of the supply device. The actual control of the instruments is by the state machine, which is described by the configuration data. The correctness of a state machine can be validated very easily. Deterministic machines are preferably used so that it is easy to verify whether the machine is working correctly. The use of state machines enables minimization of the work involved in the development of new control algorithms, thereby ensuring the safety of both the patient and the personnel operating the supply unit.

In one embodiment, the supply device has an interface for writing the configuration data into the memory device. This allows supply devices already in operation to be readily supplied with current control programs. It is very easy to provide new operating modes, for example, an operating mode for the coagulation of liver tissue.

At least one setpoint can be assigned to at least one state of the state machine, the control unit being designed such that, with control of the instrument in a control mode according to the state with the at least one setpoint control, it emits control signals to control the at least one instrument according to the setpoint. One or more setpoints can be assigned to the states of the state machine through the configuration data. This set of setpoints can define the individual states and can be processed by the control unit such that the individual instruments are operated/controlled according to these setpoints.

The supply device may include a measuring device to determine at least one sensor signal which is assigned at least one setpoint, and the control unit controlling the instrument such that the setpoint is adhered to in the main. In accordance with an embodiment, sensor signals can provide information on setting values set by the control unit, measured parameters (e.g., a tissue resistance) and supply device internal signals (e.g., a time signal). The setpoints assigned to the states are therefore used to specify certain manipulated variables and/or emit control signals, so that measured values fulfill a certain pre-specified criterion. Frequently, not all setpoints can be reached, so that the control unit must be designed such that the instrument or instruments is/are controlled close to an optimal operating point. An optimal operating point can, for example, be defined so that the sum of the amounts of the absolute error between the setpoint and actual value according to the sensor signal is as low as possible. The individual magnitude values of the errors can also be weighted.

The control unit may be designed to establish an operating point at which the respective sensor signal does not exceed the assigned setpoint.

The state machine may include at least one transition from at least one first state to at least one second state, the configuration data containing at least one transition rule and the control unit being designed such that it switches from a first control mode according to the first state to a second control mode according to the second state if the transition rule is satisfied. The presence of the transition rules can enable flexible switching between the individual states. The control unit checks the individual transition rules and initiates a transition from a first state to a second state when the transition rule is satisfied. For the control of the instrument, this means that there is a switch from a first control mode to a second control mode, the respective control mode being defined by the setpoints assigned to the states.

At least one first setpoint can be assigned to the first state and at least one second setpoint can be assigned to the second state, the first and second setpoint relating to the same sensor signal and the control unit being designed such that it captures, on the basis of configuration data, how a transfer of the sensor signal is to be made from the first setpoint to the second setpoint, and carries out a corresponding control. Usually, a certain setpoint is changed when switching between the first and second control mode. In accordance with an embodiment of the invention, the configuration data specify how a switch of the setpoint from the first value to the second value is to take place, so that corresponding control signals can be emitted to control the instrument. For example, the setpoint can be ramped up within a certain time by way of, for example, a linear equation.

The transition rules can include at least one condition that relates to at least one sensor signal. Switching between the states is thus implemented if the conditions are satisfied.

At least two transitions can be assigned to at least one state. An order can be assigned to the transitions in each case by way of the configuration data, the control unit being designed such that when controlling the instrument in a control mode according to the state with the at least two assigned transitions, the conditions of the transitions are checked according to the order. In other words, if a state has a plurality of transitions that can convert it into a subsequent state, it is possible to provide these transitions with an order. The order informs the control unit as to which transition must be checked first and is initiated if the assigned transition rule is satisfied. This allows a corresponding control program for the instruments to be more flexible.

The configuration data may include at least one control table. The state machine can be modelled relatively easily by way of a control table.

The aforementioned object is also met by a method for generating a control program for a supply device of at least one medical instrument, the method comprising the steps of: reading-in of configuration data describing a state machine with a large number of conditions; translation of the state machine with the large number of states into a control program by a control unit; and control of the at least one medical instrument according to the control program by the control unit.

This method too has similar advantages to those already described in connection with the supply device.

In particular, the software for the supply device is easier to maintain and manage. New control programs can be modelled quickly and easily. Simple graphical representations can be created that describe the programs. This can reduce the incidence of undetected logic errors. Furthermore, a strict separation can be made between the described framework program to implement the state machine and the actual state machine which is decisive for the control. The framework program that forms the basis for the control program is not changed in most cases, and acts as a sealed black box. After a successful validation of this framework program, updates of the system are very easy.

The method may include writing of configuration data of an external memory to an internal memory of the supply device. This allows the updating of the control program as described to be readily carried out.

The method for controlling the at least one instrument according to a current state from a large number of states may include the following steps: determining a sensor signal by means of a measuring device; comparing the sensor signal to a setpoint assigned to the current state; and emitting a control signal to set the sensor signal according to the setpoint.

The states of the state machine can therefore be defined, for example, by setpoints. Further advantageous embodiments are derived from the dependent claims.

BRIEF DESCRIPTION OF THE DRAWINGS

Hereinafter, exemplary embodiments of the invention are explained in greater detail with reference to the following drawings.

DETAILED DESCRIPTION

Figure 1:
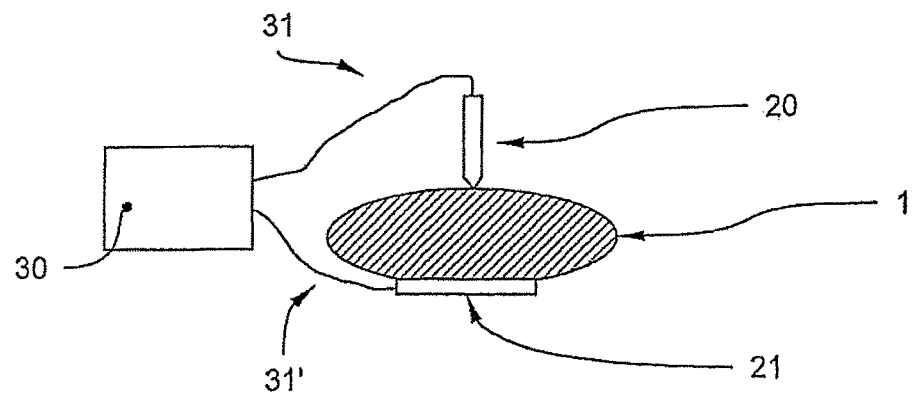
FIG. 1 illustrates a supply device with an electrosurgical instrument connected according to a disclosed embodiment.

FIG. 1 shows a supply device 30 which is connected via a first HF line 31 to an electrosurgical instrument 20. A second HF line 31' leads to a neutral electrode 21. The instrument 20 has a further electrode for the application of an HF voltage U which is provided by the supply device 30. Thus, the HF voltage U can be applied between the neutral electrode 21 and the further electrode. As shown in FIG. 1, the neutral electrode 21 and the further electrode of the electrosurgical instrument 20 can be used to introduce an HF current I into a biological tissue. FIG. 1 shows a torso 1 to which the self-adhesive neutral electrode 21 is attached. The further electrode of the electrosurgical instrument 20 is used to cut or coagulate the tissue on the other side of the torso 1.

Figure 2:
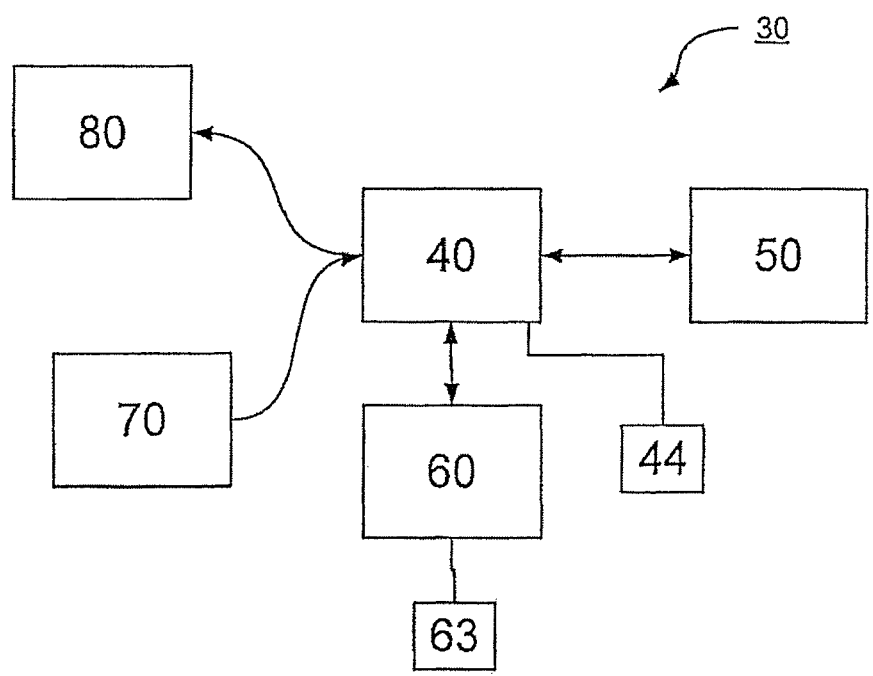
FIG. 2 illustrates individual components of the supply device according to a disclosed embodiment.

As shown in FIG. 2, the supply device 30 has a control unit 40 and an HF generator 50. The HF generator 50 serves to provide a suitable HF voltage U for the electrosurgical instrument 20 and the neutral electrode 21. The control unit 40 controls the HF generator 50 by sending control signals to the HF generator 50 and receiving sensor signals from the HF generator 50, which provide information about the state of the HF generator 50 as well as the applied HF current I and the HF voltage U. The sensor signals received can also provide information on tissue impedance R, an HF power P or a power factor cos φ. The control unit 40 is preferably designed to provide a plurality of different operating modes which, for example, have an effect on the HF voltage U or HF power P. Thus, the control unit 40 can offer a mode for coagulation and another mode for cutting tissue. In addition, further modes can be provided for different electrosurgical instruments 20 (for example, for monopolar or bipolar instruments) or for different types of tissue (liver or muscle tissue). The supply device 30 has an input unit 70, which makes it possible to receive inputs from a user of the electrosurgical instrument 20. The user can thus select a certain operating mode using the input unit 70 and activate the control unit 40 such that the HF generator 50, and thus the electrosurgical instrument 20, are operated in this operating mode. To make the selection of a particular operating mode easier, and to display status information relating to the HF generator 50 and/or the control unit 40 and/or the electrosurgical instrument 20, the supply device 30 further has an output unit 80. The output unit 80 has a screen for displaying information.

The control unit 40 is further in communicative connection with a memory unit 60, which has an interface 63 via which configuration data can be loaded into the memory unit 60. The control unit 40 has a time capture unit 44, which issues sensor signals in the form of time signals that allow the capture of predetermined time intervals.

In accordance with an embodiment of the invention, the memory unit 60 has a framework program that is executed by the control unit 40. This framework program causes the control unit 40 to load configuration data from the memory unit 60 and to generate a control program, which enables the control of the instrument 20 connected to the supply device 30. A table-controlled switching mechanism is preferably implemented here, which has a plurality of states Z0 to Z4, the individual states Z0 to Z4 being adopted depending on specified boundary conditions.

Figure 3:
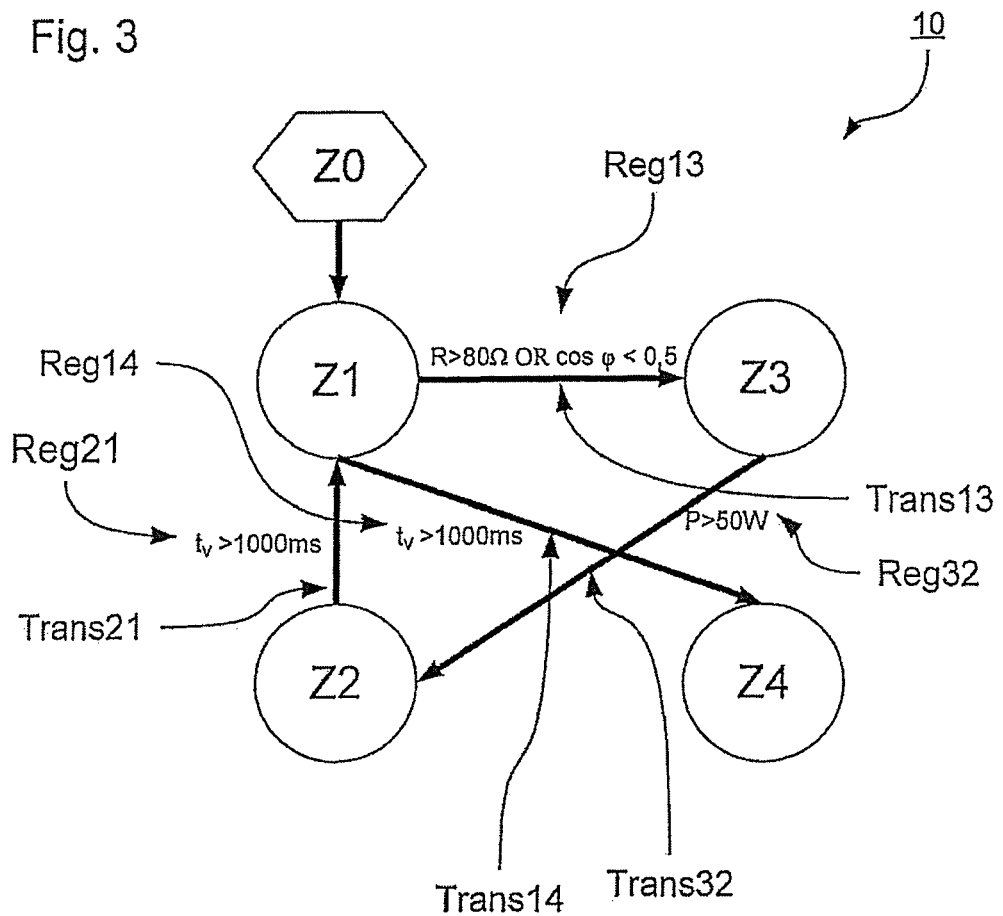
FIG. 3 illustrates a state machine for implementation by the supply device according to a disclosed embodiment.

The configuration data stored in the memory unit 60 can here model a state machine 10 in a tabular manner. A corresponding state machine 10 is shown in FIG. 3. It includes the states Z0 to Z4, the start state Z0, for example, being adopted after the selection of a certain coagulation mode. Starting from the initial state Z0, the state machine switches to a first state Z1. The state machine 10 has a plurality of transitions, Trans13, Trans14, Trans21, Trans32, which model transition to further states, namely to a second state Z2, to a third state Z3, to a fourth state Z4. The transition Trans13, for example, describes a transition from the first state Z1 into the third state Z3. Each of these transitions Trans13, Trans14, Trans21, Trans32 is assigned a transition rule Reg13/Reg14/Reg21/Reg32 respectively. The transition rule Reg13 belongs to the transition Trans13 and contains two conditions which, if satisfied, results in the control unit 40 switching from a control mode according to the first state Z1 into a control mode according to the third state Z3.

In the embodiment described in FIG. 3, the transition Trans13 is carried out when the impedance R is greater than 80 ohms or if the power factor cos φ is greater than 0.5. Transition rules Reg13, Reg14, Reg21, Reg32 are conceivable in which a condition must be maintained over a specified time period. For example, it is conceivable that the transition Trans13 is only carried out if the power factor cos φ is greater than 0.5 for more than 5 milliseconds. Starting from the first state Z1, further transitions Trans13, Trans14, Trans21, Trans32 are possible. A further transition Trans14 leads from the first state to the fourth state. The transition rule Reg14 is assigned to the transition Trans14. The transition Trans14 is carried out in accordance with the transition rule Reg14, when the control unit 40 has remained in the control mode according to the first state Z1 for longer than 1000 milliseconds (dwell time $t_v$ is greater than 1000 milliseconds). The transition Trans32 leads from the third state Z3 to the second state Z2 and is carried out according to the transition rule Reg32 when the HF power P is greater than 50 watts. The transition Trans21 leads from the second state Z2 to the third state Z3 and takes place after the second state Z2 has been adopted for a period longer than 1,000 milliseconds (exemplary condition: dwell time $t_v$ greater than 1000 milliseconds). This exemplary condition is given by the transition rule Reg21. Overall, the state machine 10 models a closed control algorithm which leads the control unit 40 from a start state Z0 through several intermediate states Z1, Z2, Z3 to a final state, namely the fourth state Z4.

Each of the states Z1 to Z4 is preferably assigned setpoints in tabular form: An exemplary setpoint set for state ZI is: U=200 V; I=3 A; and P=120 W. An exemplary setpoint set for state Z2 is: U=350 V; I=1 A; and P=300 W. An exemplary setpoint set for state Z3 is: U=500 V; I=1 A; and P=120 W. An exemplary setpoint set for state Z4 is: U=250 V; I=3 A; and P=90 W.

The control unit 40 may be configured such that the individual setpoints are set as the control values. For example, the control unit 40 can emit control signals to the HF generator 50, which set it so that the setpoints are met. It is frequently the case, however, that operation of the supply device 30 at the given setpoints is not possible. For these cases, the control unit 40 is configured to establish operating points at which settings or measured values are achieved that are as close as possible to the specified setpoints.

In the aforementioned embodiment, a plurality of transitions, namely the transitions Trans13 and Trans14, result from the first state Z1. It is possible to assign priorities to the individual transitions Trans13, Trans14 so that they are checked by the control unit 40 in a given order. For example, the transition Trans13 can be checked before the transition Trans14. If, therefore, the conditions according to the transition rule Reg13 are satisfied at a given time at which the control unit 40 is in a control mode according to the first state Z1, then the control unit will immediately switch to a control mode according to the third state Z3. The transition rule Reg14 is checked only if the conditions of the transition rule Reg13 are not satisfied.

In general, a control machine/state machine (i.e., device) in accordance with an embodiment of the invention can be parameterized through a control table, which may include: (1) Start setting: for example, with a setpoint for the start state Z0; (2) Further states as resulting states: for example, the states ZI to Z4; (3) Transitions: exemplary transitions Trans13, Trans14, Trans21, Trans32; and (4) Transition conditions: exemplary transition rules Reg13, Reg14, Reg21, Reg32.

The transition conditions can relate to thresholds or changes of slope of measured variables or to absolute values (for example, R greater than 200 ohms) or to relative values (for example, R greater than 10% of the last value measured). Alternatively, frequencies (for example, in how many measurements was R greater than 200 ohms) or time interval (for example, dwell time $t_v$=300 milliseconds) can be taken into account. The transition conditions can also include combinations of transition conditions (for example, logical AND/OR operations).

An example of a control table for the instrument 20 is shown below, which essentially corresponds to the configuration of FIG. 3. The time frame of the jump conditions=I00 μs.

| Basic Setting |
| --- |
| U_HF max [V peak] = 200 |
| I_HF max [A rms] = 3 |
| P_HF max [W] = 120 |
| RiGenerator [Ohm] = 0 |
| Funke [V] = 0 |
| Signals, relay = Cut/Coag CW |
| U_Nt max [V]: = 200 |
| I_Nt max [A] = 2.5 |
| APC argon [l/min] = 0 |
| APC Preflow [s] = 0 |

| State 1: Start |
| --- |
| –> U_HF max = 200 V peak |
| –> I_HF max = 3 A rms |
| –> P_HF max = 120 W |
| Jump 1A >>> Resistance exceeded <<< |
| Jump 1A: If Rload >= 80 ohms once, then switch to state 3 |
| Jump 1B >>> cos phi < 0.5 (= LF 16384) <<< |

State 1: Start

Jump 1B: When LF < 16384 fifty times, then switch to state 3
Jump 1C >>> Time limit <<<
Jump 1C: If 10,000 times, then switch to state 4

State 2: State 2

-> U_HF max = 350 V peak
-> I_HF max = 1 A rms
-> P_HF max = 300 W
Jump 2A >>> Wait 1 second <<<
Jump 2A: If 10,000 times, then switch to state 3

State 3: State 3

-> U_HF max = 500 V peak
-> I_HF max = 1 A rms
-> P_HF max = 120 W
Jump 3A >>> Power exceeded <<<
Jump 3A: If P_HF > 50 W once, then switch to state 2

State 4: State 4

>>> Stable state up to end of activation <<<
-> U_HF max = 250 V peak
-> I_HF max = 3 A rms
-> P_HF max = 90 W In the preceding embodiments, control programs for electrosurgical instruments were described to illustrate the invention. However, it should be apparent to a person skilled in the art how the invention can be used to control cryosurgical instruments and/or water jet surgical instruments.

In this context, it must also be noted that the setpoints may also relate to mechanical activities, such as activation and deactivation of a valve. For example, a setpoint may relate to the opening or closing of a valve. Furthermore, it is conceivable that a setpoint relates to a position in a three-dimensional coordinate system to which a device, for example a robot arm, is to move. The setpoint can also indicate that the tip of an electrosurgical instrument is extended or retracted. Thus, the individual states can be linked to a plurality of mechanical activities which are carried out by the electrosurgical instrument or the supply device.

The invention claimed is:

1. A supply device for operating an RF generator for supplying at least one medical instrument, the supply device comprising:
a memory unit for storing a framework program and configured to store configuration data representing at least one state device, each state device corresponding to a different one of a plurality of operation modes of the RF generator, having a plurality of states, and assigning at least one setpoint to at least one state of the respective state device; and
a control unit for executing the framework program in order to read in the configuration data, and control the RF generator according to the plurality of operation modes.

2. The supply device of claim 1, wherein the at least one medical instrument is selected from the group consisting of an electrosurgical instrument, a cryosurgical instrument, a water jet surgical instrument and a combination thereof.

3. The supply device of claim 1, further comprising:
an interface configured to write the configuration data to the memory unit.

4. The supply device of claim 1, wherein the configuration data comprises at least one control table.

5. The supply device of claim 1, wherein the control unit is configured to control the at least one medical instrument by emitting control signals to control the at least one medical instrument according to the at least one setpoint.

6. The supply device of claim 5, further comprising:
a measurement unit for measuring at least one sensor signal to which is assigned the at least one setpoint, the control unit configured to control the at least one medical instrument such that the setpoint is substantially maintained.

7. The supply device of claim 6, wherein the control unit is configured to establish an operating point at which the at least one sensor signal does not exceed the assigned at least one setpoint.

8. The supply device of claim 6, wherein:
the state device comprises at least one transition of at least one first state into at least one second state,
the configuration data comprises at least one transition rule, and
the control unit is further configured to switch from a first control mode according to the at least one first state into a second control mode according to the at least one second state when the at least one transition rule is satisfied.

9. The supply device of claim 8, wherein:
at least one first setpoint is assigned to the at least one first state and at least one second setpoint is assigned to the at least one second state,
the at least one first setpoint and the at least one second setpoint relating to the same sensor signal, and
the control unit is further configured to:
capture, based on the configuration data, how a transfer of the sensor signal from the at least one first setpoint to the at least one second setpoint has to occur, and
undertake a corresponding control operation.

10. The supply device of claim 8, wherein the at least one transition rule comprises at least one condition relating to at least one sensor signal.

11. The supply device of claim 10, wherein:
at least two transitions are assigned to the at least one state by the configuration data,
an order is assigned to each of the at least two transitions by the configuration data, and
the control unit is further configured to, when controlling the at least one medical instrument in a control mode according to the state with the at least two transitions, check the at least one condition of the at least two transitions according to the order.

12. The supply device of claim 1, wherein the plurality of operation modes comprises at least one of cutting mode, coagulation mode, monopolar instrument mode, bipolar instrument mode and a mode based on tissue type.

13. A method for controlling an RF generator for supplying at least one medical instrument, the method comprising:
reading into a framework program configuration data that represents at least one state device, each state device corresponding to a different one of a plurality of operation modes of the RF generator and having a plurality of states;
assigning at least one setpoint to a current state of the plurality of states by the configuration data; and using the framework program to control the RF generator according to the plurality of operation modes.

14. The method of claim 13, wherein the at least one medical instrument is selected from the group consisting of an electrosurgical instrument, a cryosurgical instrument, a water jet surgical instrument and a combination thereof.

15. The method of claim 13, further comprising:
writing configuration data of an external memory to an internal memory of the supply device.

16. The method of claim 13, further comprising:
measuring a sensor signal with a measuring device;
comparing the sensor signal with the setpoint assigned to the current state; and
emitting a control signal to set the sensor signal according to the setpoint.

17. The method of claim 13, wherein the plurality of operation modes comprises at least one of cutting mode, coagulation mode, monopolar instrument mode, bipolar instrument mode and a mode based on tissue type.

18. A method for controlling an RF generator for supplying at least one medical instrument, the method comprising:
reading into a framework program configuration data that describe a represents at least one state device, each state device corresponding to a different one of a plurality of operation modes of the RF generator and having a plurality of states;
using the framework program to control the RF generator in a current state of a current operation mode by:
assigning at least one transition rule to the current state;
measuring at least one sensor signal with a measuring device;
comparing the at least one sensor signal with the at least one transition rule assigned to the current state;
when the at least one transition rule is satisfied, determining a next state; and
controlling the RF generator according to the next state.

19. The method of claim 18, wherein the at least one transition rule comprises a plurality of conditions that each relate to a sensor signal.

20. The method of claim 18, wherein the plurality of operation modes comprises at least one of cutting mode, coagulation mode, monopolar instrument mode, bipolar instrument mode and a mode based on tissue type.

* * * * *